United States Patent [19]
Burri et al.

[11] Patent Number: 5,717,486
[45] Date of Patent: Feb. 10, 1998

[54] PROCESS FOR REMOVING RETURNABLE CONTAINERS FROM CIRCULATION UTILIZING IMAGE PROCESSING OF BRIGHTNESS VALUES FOR INSPECTION WINDOWS

[75] Inventors: Karl-Georg Burri, Oberrieden, Switzerland; Petr Pavlik, Prag, Czech Rep.

[73] Assignee: Elpatronic AG, Zug, Switzerland

[21] Appl. No.: 713,098

[22] Filed: Sep. 16, 1996

Related U.S. Application Data

[63] Continuation of Ser. No. 373,601, Jan. 17, 1995, abandoned.

[30] Foreign Application Priority Data

Jan. 21, 1994 [CH] Switzerland .......... 00 188/94

[51] Int. Cl.[6] .......... G01N 21/00; G01N 9/04; B07C 5/00
[52] U.S. Cl. .......... 356/240; 356/427; 250/223 B; 382/142; 348/127; 209/576; 209/588
[58] Field of Search .......... 356/240, 427; 250/223 B; 209/524, 576–577, 588; 348/91, 127, 132; 382/142

[56] References Cited

U.S. PATENT DOCUMENTS

| | | | |
|---|---|---|---|
| 3,770,969 | 11/1973 | Ausevin et al. | 250/223 B |
| 4,435,641 | 3/1984 | Hajime | 250/223 B |
| 4,448,526 | 5/1984 | Miyazawa | 250/223 B |
| 4,606,635 | 8/1986 | Miyazawa et al. | 348/127 |
| 4,959,537 | 9/1990 | Kimoto et al. | 250/223 B |
| 5,305,391 | 4/1994 | Gomibuchi | 382/142 |
| 5,405,015 | 4/1995 | Bhatia et al. | 209/524 |
| 5,466,927 | 11/1995 | Kohler et al. | 356/240 |
| 5,510,610 | 4/1996 | Baldwin | 356/240 |

FOREIGN PATENT DOCUMENTS

| | | | |
|---|---|---|---|
| 0 472 881 | 3/1992 | European Pat. Off. | |
| 0 483 966 | 5/1992 | European Pat. Off. | |
| 0 540 018 | 5/1993 | European Pat. Off. | |
| 04309850 | 11/1992 | Japan | 348/127 |

*Primary Examiner*—Frank G. Font
*Assistant Examiner*—Jason D. Vierra Eisenberg
*Attorney, Agent, or Firm*—McCormick, Paulding & Huber

[57] ABSTRACT

To detect damage in the bottom region of a plastic bottle a picture of the bottom region is taken by means of a camera. The resulting image is then tested for brightness pixel by pixel in a predetermined inspection area. Large deviations of the test curve from the average value are indicative of a damaged bottle. The process is meaningful, and it can be carried out on existing bottle inspection machines.

14 Claims, 1 Drawing Sheet

PROCESS FOR REMOVING RETURNABLE CONTAINERS FROM CIRCULATION UTILIZING IMAGE PROCESSING OF BRIGHTNESS VALUES FOR INSPECTION WINDOWS

This is a continuation of application Ser. No. 08/373.601 filed on Jan. 17, 1995 (now abandoned).

BACKGROUND OF THE INVENTION

The invention relates to a process for the inspection of returnable containers, especially returnable plastic bottles, in multi-trip use, in which, basically every time the container is returned, an image is recorded of a region of the container, especially of the container bottom, by image recording apparatus, and is analysed automatically.

It is a known procedure optically to inspect incoming used returnable bottles for the presence of heavy contamination or foreign bodies, by analysis of a picture of the interior of the bottle which is taken by a camera. Depending on the outcome of the inspection, bottles are removed from circulation or left in circulation.

With returnable plastic bottles in particular, eg. PET bottles, which have a limited life, the problem arises that bottles coming to the end of their life owing to so-called stress cracks need to be taken out of circulation promptly, not only for reasons of visual appearance and hygiene, but also to ensure that bottles do not fracture or split while in use by the consumer, and also to avoid splitting or bursting of bottles in the bottling plant during the refilling operation, in the course of which an individual bottle is subjected to relatively high pressure. Hitherto no way has been found of detecting the usual fatigue damage of such bottles (appearing especially in the form of fine, more or less deep, radial and azimuthal cracks in the bottom of the bottles) in such a way that the degree of damage, and in particular the end of the bottle's life, can be identified. The cracks develop during the life of the bottle as a result of cleaning and transport, and in particular as a result of individual handling by the user. The prevalence and depth of the cracks increase during the life of the bottle, which is largely determined by the presence of the cracks.

The object, therefore, is to make it possible to ascertain the condition of the bottle and in particular to remove bottles from circulation promptly before they reach the end of their service life, but without taking bottles out of circulation unduly prematurely. The object, moreover, is to accomplish this cheaply and rapidly in an industrial setting (modern bottle inspection systems attain a throughput of 40,000 to 60,000 bottles per hour).

SUMMARY OF THE INVENTION

The present invention relates to a process and apparatus for inspecting returnable containers, especially returnable plastic bottles, in the course of their circulation. Substantially every time a container is returned, an image is recorded of a region of the container, especially the container bottom, by means of an image recording apparatus and is then analyzed. The image analysis includes at least one evaluation process for the detection of cracks in a container region in which an inspection area is defined. The inspection area is split into a plurality of inspection windows whose brightness is determined. The sequence of brightness values is evaluated in order to detect on the basis of the image analysis a particular stage of the condition of the container. If necessary, the container is removed from circulation when damage is identified.

The invention afford a means of measuring crack prevalence and crack depth. Thus the bottle can be removed before critical levels are reached. The use of image analysis to achieve this aim means that in principle recourse can be had to existing contamination and foreign-body detection systems which have been proven in an industrial context, thus making the solution very inexpensive. Since use is made of an image which is being recorded anyway, the process involves no additional inspection step on the bottle itself, so that the bottle throughput need not be affected in any way.

BRIEF DESCRIPTION OF THE DRAWINGS

Further aspects of the invention will now be explained in detail with reference to the drawings, in which.

DESCRIPTION OF THE PREFERRED EMBODIMENTS

Figure 1:
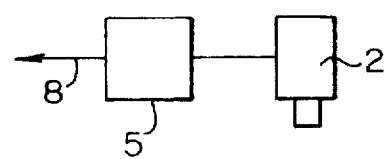
FIG. 1 shows schematically one possible arrangement of camera, bottle and lighting for carrying out the process.

FIG. 1 schematically depicts a plastic bottle 1, assumed to be in a bottle inspection machine which is not illustrated in detail. Such inspection machines are known and do not need to be explained in detail here. In particular they have a conveyor system for carrying the bottles, usually in an upright position, to various inspection stations. FIG. 1 represents such an inspection station in which a picture of the bottle bottom is taken by a camera 2. For this purpose, in the example shown, homogeneous and preferably diffuse illumination of the domed bottom 3 of the bottle is provided by means of a photoflash arrangement 6, comprising eg. flash lamps or pulsed LED arrays. Alternatively, steady lighting in conjunction with a camera shutter may be used. In the example shown, the bottle 1 stands with its circular base surface 4 resting on a transparent stand surface 7. Alternatively, the bottle may be conveyed and/or held differently so that the stand surface 7 is not necessary. The video camera 2 takes the picture generated by the illumination. The image is fed to a computer 5 where it is analysed. Based on the result of the analysis, a control signal can be output via a line 8 to an ejector or deflector device (not shown) which removes the bottle when it subsequently arrives at some point along the conveyor path, if this is dictated by the analysis result. As already stated, gross contamination or foreign bodies inside the bottles have hitherto been detected by such methods.

The present invention comes into play in the interpretation of the image which has been stored in memory. This may be a picture which has, as described, been taken for the purpose of bottom inspection or for some other purpose, and/or which has been taken from any point from which the bottom is visible.

The fundamental idea is based on the fact that the transparent, illuminated bottle bottom transmits light which then passes into the sensor (camera). Stress cracks interfere with the transmission of light, resulting in eg. a darkening of the image at the location of the stress crack. An image is formed when a ray of light from the light source passes through the bottom and arrives at the sensor (or vice versa, as it is only the closed path between the two that matters).

This light path is not straight, but follows a zigzag course owing to refraction on transition from one medium to another.

In the preferred way of carrying out the invention, the image is then processed as follows: Determination of the centre and of the base surface of the bottle (an annular surface). Definition of an inspection area, normally by defining a circle with a radius smaller than that of the base surface. A circle width of one pixel is sufficient; but, to eliminate interference, a circular ring with a width of several pixels is preferably scanned.

Preferably, the annular inspection area is approximately 3 mm wide and adjoins the base surface on the side towards the centre of the bottom of the bottle. The value of approximately 3 mm is especially preferred for 1.5 liter bottles. Surprisingly, this has proved to be the best region for detecting stress cracks even though the highest density of stress cracks does not occur in this region. It is a region which in practice presents itself as essentially free from interference (ie. free from water drops and from the fogging referred to as "haze"), and as one in which the stress cracks are easily visible. For bottle sizes other than 1.5 liters, the value may vary from the 3 mm stated, and can be determined on the basis of the abovementioned criteria. The inspection area can of course be shifted to another region, but the evaluation of the image will then be more complicated, and as a rule slower.

The evaluation is made by placing an observation window on the circle and analysing it, and then shifting it and analysing it again. The results of the evaluation can be presented as a curve over the circumference of the circle. What is actually evaluated is the brightness, or the change in brightness from one window position to the next.

The shift of the windows in the inspection area is preferably such that successive windows overlap. The windows may have eg. a width of 3 pixels (in the radial direction) and a length of 4 to 10 pixels (in the circumferential direction).

Figure 2:
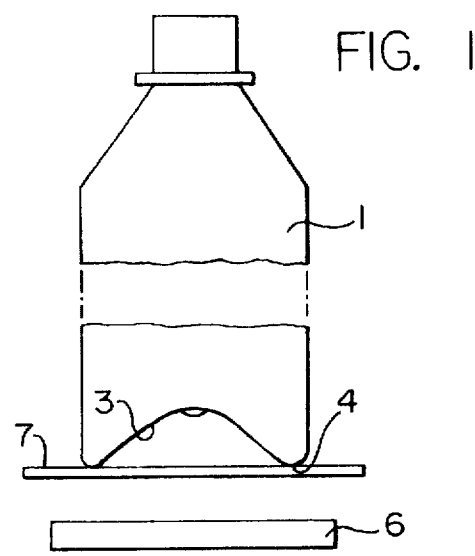
FIG. 2 shows schematically the resulting image of the bottle bottom, with inspection windows and radii drawn in for the purpose of illustration.
Figure 2:
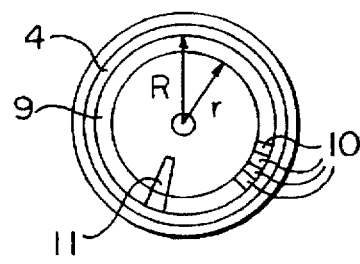

FIG. 2 shows schematically the image of the bottle bottom with base surface 4. In FIG. 2, the inspection area 9 is shown immediately adjacent to the base surface 4. The inner radius of the base surface 4 is denoted by R and the inner radius of the inspection area by r, with the inspection width R-r equal to the preferred value of 3 mm. Alternatively the inspection area may be shifted further towards the centre of the bottle, possibly leaving a gap between it and the base surface 4. The inspection area may also consist of a number of annular segments; but it is preferable to define a complete ring (360°) as the inspection area.

In FIG. 2 a number of inspection windows 10 are represented highly schematically on an enlarged scale to facilitate the description of the invention. The preferred overlapping of windows has not been shown.

In each window a different image brightness may be detectable, depending on the stress cracks picked up in the image. A stress crack will have a surface whose slope is different from that of the undamaged surface. Consequently light emerges in a different direction. This usually results in disruption of the path of the ray of light from the light source so that it is no longer aimed at the camera but at some other point. Stress cracks therefore show up as a change in contrast. Alternatively, the system could make use of another effect: with the camera in the dark field, the path from light source to camera is closed at the location of the stress cracks. Such effects may also occur only for individual frequencies of light of mixed frequencies.

If an observation window is for example much wider than a small crack but only slightly wider than a large crack, a small crack yields only a relatively slight deviation from the normal brightness in the window, and the response of the curve stays around the mean value. When the window lies directly over a large crack, its condition changes sharply, resulting in a sharp response on the curve.

Soiling also produces such responses. Accordingly, significant stress cracking is not inferred unless large numbers of sharp responses occur (around the circle of 360°). Again, where the presence of a major stress crack is suspected, a radial observation window may be opened to check whether or not the anomaly possesses a geometry similar to that of a stress crack. Such a window is schematically indicated in FIG. 2 as the window 11.

It is also helpful to integrate the signal curve over 360°; a generally dark average level, even if the responses of the curve are small, implies a generally defective surface (with stress cracks or hazing) which will then be similarly classed as "unacceptable", even though the individual major responses which are indicative of unacceptably-large stress cracks are themselves absent.

Figure 3:
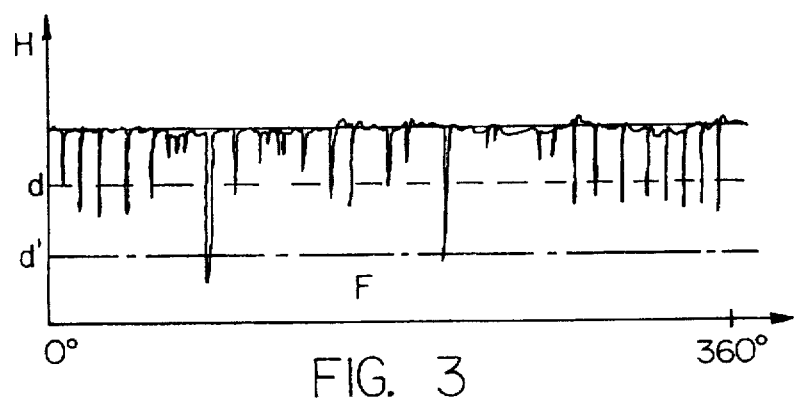
FIG. 3 shows in simplified form a brightness distribution along the inspection area.

FIG. 3 shows in greatly coarsened form the signal curve corresponding to the brightness H along the 360° inspection area. The straight line is intended to represent the normal or average level of brightness of the image. Large downward deviations of the curve, below eg. a limit value d, are symptomatic of major stress cracks, as has already been stated. If these downward deviations occur in relatively large numbers, the bottle is to be removed as unacceptable. Also, isolated particularly large deviations, which fall below eg. a second limit value d', can give a similar result. Moreover, the extent of the area F below the curve can also, as described, be adopted as a criterion.

In the case of PET bottles, there exist in particular two principal types of damage. Firstly, there are bottles which possess a small number of coarse cracks randomly spaced apart from one another. These bottles show up as highly transparent, with a few generally dark spots. Secondly, there are bottles which exhibit a large number of fine cracks. Besides these basic types, of course, bottles are also encountered which possess both types of damage to a greater or lesser degree. It has proved particularly advantageous for the interpretation of the image if the number of occasions when individual limit values, eg. the two limits d and d' of FIG. 3, are exceeded are separately weighted and then summed. Thus, the number of occasions when the limit d is exceeded is determined. This number is multiplied by a weighting factor g1. The number of occasions when the limit d' is exceeded is also established. This number is multiplied by a weighting factor g2. The weighted numbers are added together and their sum is compared with a rejection-value which can be selected at will. If the sum-value reaches or surpasses the rejection-value, the bottle is removed. From the sum-values obtained, it is also possible to compile statistics on the condition of the bottles inspected.

In a further way of carrying out the invention, a non-visible form of radiation may be used instead of visible light. Like visible light, this will be refracted as it passes through the bottle wall. With a suitable recording apparatus, a crack can then be recorded in the same way as when visible light is used. Depending on their characteristics, individual frequencies or mixtures of frequencies may be used. Another configuration within the scope of the invention has an analysing arrangement for carrying out the process according to the invention in which defects can be detected anywhere on the bottle (eg. in the neck region). The bottle regions to be inspected are photographed directly or indirectly, eg. by mirrors, by the image recording apparatus, after which, instead of a ring (as in the case of the bottom region), some other segment is analysed by the evaluation unit.

What is claimed is:

1. Process for the inspection of returnable bottles, in the course of circulation, comprising the steps of:

transmitting light through the bottom of a bottle to be inspected recording an image of the bottle bottom using an image recording arrangement and the light transmitted through the bottle bottom, the bottle bottom having an annular, lowermost, base surface about the center axis of the bottle and on which the bottle rests in an upright position;

defining an inspection area of the image generated by the image recording arrangement, the inspection area defining at least an annular segment about the bottle center axis and disposed inwardly of the base surface;

dividing the inspection area into a plurality of sequential inspection windows;

determining individual brightness values for each inspection window of the plurality of sequential inspection windows;

determining an average brightness value of the inspection area using the brightness values of the inspection windows over the inspection area;

determining the amount of the deviation of the brightness values of each of the inspection windows from the average brightness value of the inspection area;

determining the number of deviations which deviate by an amount greater than a predetermined amount; and removing the bottle from circulation based upon the number of deviations which deviate by an amount greater than a predetermined amount.

2. Process according to claim 1, characterized in that the annular segment has a width in the radial direction of approximately 3 mm.

3. Process according to claim 1, characterized in that each inspection window has a width in the radial direction corresponding to a few pixels of the image recording arrangement.

4. Process according to claim 1, wherein during the step of dividing the inspection area into a plurality of inspection windows, the inspection windows are defined such that adjacent inspection windows overlap one another.

5. Process according to claim 1, further comprising the steps of:

defining an additional inspection window of the image if it is determined during the step of determining the amount of the deviation that the deviation between an inspection window brightness and the average brightness value of the inspection area is greater than a preselected value, the additional inspection window being elongated radially from the inspection window for which the brightness value deviates from the average brightness value by greater than a preselected value towards the center axis of the bottle; and determining an individual brightness value for the additional inspection window.

6. Process according to claim 1, further comprising the step of:

producing a signal curve from the individual brightness values of the inspection windows;

wherein the steps of determining the average brightness of the inspection area, determining the amount of the deviation, and determining the number of deviations are performed using the signal curve.

7. Process according to claim 6, further comprising the step of:

integrating the signal curve, and performing the steps of determining the average brightness of the inspection area, determining the amount of the deviation, and determining the number of deviations using the integrated signal curve.

8. Process according to claim 1, wherein the predetermined amount is a first predetermined amount, the step of determining the number of deviations further includes the steps of:

determining the number of deviations which deviate by an amount greater than a second predetermined amount, weighting the number of occasions when the deviation exceeds the first and second predetermined amounts differently to obtain a weighted number of deviations, and summing the weighted number of deviations wherein the step of removing is performed using the summed, weighted number of deviations.

9. Apparatus for the inspection of returnable bottles in the course of circulation, comprising:

a bottle conveyor for moving returnable bottles along a conveyor path;

a light source for projecting light through the bottoms of bottles on the conveyor;

at least one image recording arrangement arranged along the conveyor for recording an image of a bottle bottom using light transmitted from the light source and through the bottle bottom, each bottle bottom having a center axis and a generally annular base surface around the axis and on which the bottle rests in an upright position;

an image evaluation unit coupled to the image recording arrangement and including at least one computer, the evaluation unit also including means for defining an inspection area of the image generated by the image recording arrangement, the inspection area including at least an annular segment about the bottle center axis and within the annular base surface, means for dividing the inspection area into a plurality of sequential inspection windows, means for determining individual brightness values of each of the plurality of sequential inspection windows, means for determining an average brightness value of the inspection area using the brightness values of the plurality of inspection windows, means for determining the deviation of each of the brightness values from the average brightness value, and means for determining the number of deviations greater than a predetermined amount and generating a signal output when the number exceeds a predetermined number; and at least one deflector device triggered by the signal output of the evaluation unit for removing containers from the conveyor path.

10. Apparatus according to claim 9, characterized in that the light source is for homogeneous illumination of the container bottom.

11. Process for the inspection of returnable bottles, in the course of circulation, comprising the steps of:

transmitting light through the bottom of a bottle to be inspected;

recording an image of the bottle bottom using an image recording arrangement and the light transmitted through the bottle bottom, the bottle bottom having an annular, lowermost, base surface about the center axis of the bottle and on which the bottle rests in an upright position;

defining an inspection area of the image generated by the image recording arrangement, the inspection area defining at least an annular segment about the bottle center axis and disposed inwardly of the base surface;

dividing the inspection area into a plurality of sequential inspection windows;

determining individual brightness values for each inspection window of the plurality of sequential inspection windows;

generating a signal curve for the inspection area using the brightness values of each inspection window of the inspection area;

evaluating the signal curve as a measure of the condition of the bottle; and removing the bottle from circulation based upon the result of the step of evaluating.

12. Process according to claim 11, further comprising the step of:

integrating the signal curve, and wherein the step of evaluating includes the step of evaluating the integrated signal curve.

13. Process for the inspection of returnable bottles, in the course of circulation, comprising the steps of:

transmitting light through the bottom of a bottle to be inspected;

recording an image of the bottle bottom using an image recording arrangement and the light transmitted through the bottle bottom, the bottle bottom having an annular, lowermost, base surface about the center axis of the bottle and on which the bottle rests in an upright position;

defining an inspection area of the image generated by the image recording arrangement, the inspection area defining at least an annular segment about the bottle center axis and disposed inwardly of the base surface;

dividing the inspection area into a plurality of sequential inspection windows;

determining individual brightness values for each inspection window of the plurality of sequential inspection windows;

determining an average brightness value of the inspection area using the brightness values of the inspection windows over the inspection area;

determining whether the brightness values for each inspection window is below the average brightness value; p1 determining the amount of the deviation of the brightness values of each of the inspection windows from the average brightness value of the inspection area only for those inspection windows which have an individual brightness value below the average brightness value;

determining the number of deviations which deviate below the average value by an amount greater than a predetermined amount; and removing the bottle from circulation based upon the number of deviations which deviate by an amount greater than a predetermined amount.

14. Process for the inspection of returnable bottles, in the course of circulation, comprising the steps of:

transmitting light through the bottom of a bottle to be inspected;

recording an image of the bottle bottom using an image recording arrangement and the light transmitted through the bottle bottom, the bottle bottom having an annular, lowermost, base surface about the center axis of the bottle and on which the bottle rests in an upright position;

defining an inspection area of the image generated by the image recording, arrangement, the inspection area defining at least an annular segment about the bottle center axis and disposed inwardly of the base surface;

dividing the inspection area into a plurality of sequential inspection windows;

determining individual brightness values for each inspection window of the plurality of sequential inspection windows;

determining an average brightness value of the inspection area using the brightness values of the inspection windows over the inspection area;

determining the deviation between the average brightness value of the inspection area and a predetermined value; and removing the bottle from circulation based upon the deviation of the average brightness and the predetermined value.

* * * * *